US006358511B1

(12) United States Patent
Klotman et al.

(10) Patent No.: US 6,358,511 B1
(45) Date of Patent: Mar. 19, 2002

(54) INHIBITORS OF HIV INFECTION

(75) Inventors: Mary E. Klotman, New York; Mosoian Arevik, Elmhurst, both of NY (US); Teixeira Avelino, Montclair, NJ (US)

(73) Assignee: Mount Sinai School of Medicine of the City University of New York, New York, NY (US)

( * ) Notice: Subject to any disclaimer, the term of this patent is extended or adjusted under 35 U.S.C. 154(b) by 0 days.

(21) Appl. No.: 09/305,781

(22) Filed: May 3, 1999

(51) Int. Cl.$^7$ ............................................. A01K 37/18
(52) U.S. Cl. .................... 424/185.1; 530/327; 530/328
(58) Field of Search .......................... 435/5, 7.1, 7.2, 435/7.24, 243; 530/327, 328; 424/185.1

(56) References Cited

U.S. PATENT DOCUMENTS 5,627,023 A * 5/1997 Bolognesi et al. ............. 435/5

OTHER PUBLICATIONS

Mackewicz et al., Cell. Immunol. 153:329–343, 1993.
Blackbourn et al., Proc. Natl. Acad. Sci. USA 93:13125–13130, 1996.
Mackewicz et al., J. Clin. Invest. 87:1462–1466, 1991.
Deng et al., Nature 381:661–666, 1996.
Dragic et al., Nature 381:667–673.
Feng et al., Science 272:872–877, 1996.
Doranz et al., Cell 85:1149–1158, 1996.
Marcon et al., J. Virol. 71:2522–2527, 1997.
Chen et al., J. Virol. 71:2705–2714, 1997.
Oberlin et al., Nature 382:833–835, 1996.
Liao et al., J. Exp. Med. 185:2015–2023, 1997.
Liu et al., Cell 86:367–377, 1996.
Dean et al., Science 273:1856–1862, 1996.
Huang et al., Nature Med. 2:1240–1243, 1996.
Smith et al., Science 277:959–965, 1997.
Kotler et al., Proc. Natl. Acad. Sci. 85:4185–4189, 1985.
Aldrovandi et al., J. Virol. 70:1505, 1996.
Weber et al., Proc. Natl. Acad. Sci. USA 90:11049–11053, 1993.
Biesinger et al., Proc. Natl. Acad. Sci. USA 89:3116–3119, 1992.
Chen et al., AIDS Res. Human Retroviruses 9(11):1079–1086, 1993.
Cocchi et al., Science 260:1811–1815, 1995.
Walker et al., J.Virol.65:5921–5927, 1991.
Deng et al., Nature 388:296–300, 1997.
Mackewicz et al., Proc. Natl. Acad.Sci.USA 92:2308–2312, 1995.
Paliard et al., AIDS 10:1317–1321, 1996.
Walker et al., Science 234:1563–1566, 1986.
Pal et al., Science 278:695–698, 1997.
Kledal et al., Science 277:1656–1659, 1997.
Moriuchi et al., Proc.Natl.Acad. Sci.USA 93:15341–15345, 1996.

* cited by examiner

*Primary Examiner*—Jeffrey Stucker
(74) *Attorney, Agent, or Firm*—BakerBotts LLP

(57) ABSTRACT

The present invention is directed to novel inhibitory compounds which are capable of reducing, eliminating, or preventing human immunodeficiency virus (HIV) infection. These compounds may be polypeptides or peptides comprising particular sequences that inhibit HIV-1 infection. These compounds may be derived from CD8+ lymphocytes. The invention is also directed to novel CD8+ cell lines which secrete these novel inhibitors. The invention is further directed to compositions comprising an inhibitor of the invention and to methods for the use of such compositions in the prevention and/or treatment of HIV infection.

2 Claims, 10 Drawing Sheets

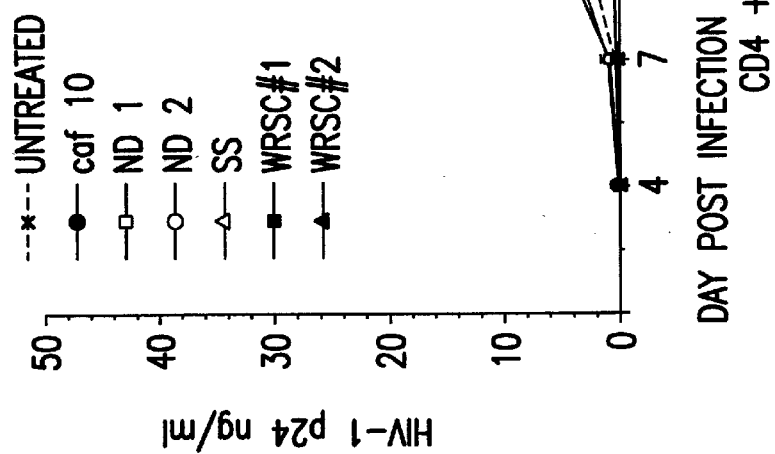
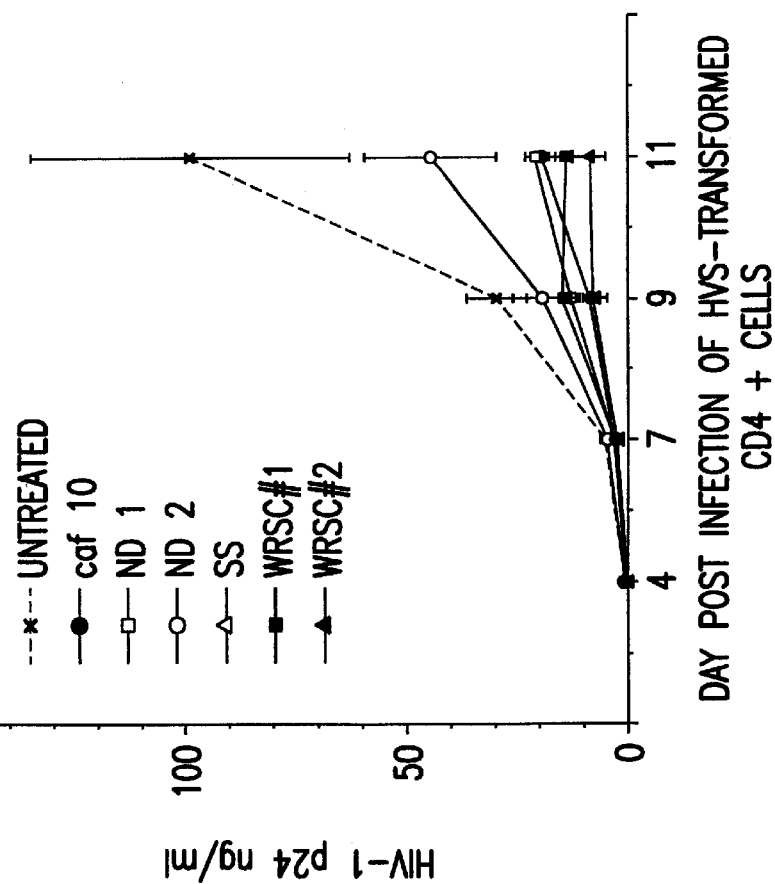
FIG. 2B
FIG. 2A

SEQUENCE LISTING

```
<160> NUMBER OF SEQ ID NOS: 2

<210> SEQ ID NO: 1
<211> LENGTH: 9
<212> TYPE: PRT
<213> ORGANISM: Human

<400> SEQUENCE: 1

Glu Gln Val Glu Ala Ser Val Ala Ser
 1              5

<210> SEQ ID NO: 2
<211> LENGTH: 14
<212> TYPE: PRT
<213> ORGANISM: Human
```

```
<400> SEQUENCE: 2

Glu Gln Val Glu Ala Ser Val Ala Ser Val Arg Ser Leu Tyr
1               5                   10
```

INHIBITORS OF HIV INFECTION

INTRODUCTION

The present invention is directed to novel inhibitory compounds which are capable of reducing, eliminating or preventing human immunodeficiency virus (HIV) infection and which are isolated from CD8+ lymphocytes. The invention is also directed to CD8+ cell lines which secrete these novel inhibitors. The invention is further directed to compositions comprising an inhibitor of the invention and to methods for the use of such compositions in the prevention and/or treatment of HIV infection.

BACKGROUND OF THE INVENTION

CD8+ cells from HIV-1 infected individuals exhibit HIV-1 inhibitory activity that is not MHC-restricted and is non-cytolytic (Walker et al., Science 234:1563–1566, 1986; Walker et al., J. Virol. 65:5921–5927, 1991; Mackewicz et al., Cell. Immunol. 153:329–343, 1993). The inhibition does not require cell to cell contact and is mediated through soluble factors, hence the original name CD8+-cell antiviral factors (CAF, Walker et al., J. Virol. 65:5921–5927, 1991). Further studies suggested that CD8+ CAF activity correlated with the clinical status of an infected individual (Blackbourn et al., Proc. Natl. Acad. Sci. USA 93:13125–13130, 1996; Mackewicz et al., J. Clin. Invest. 87:1462–1466, 1991). The mechanism of action of this activity, as originally described, was thought, at least partially, to be through the inhibition of Tat-induced transcription (Mackewicz et al., Proc. Natl. Acad. Sci. USA 92:2308–2312, 1995; Chen et al., AIDS Res. Human Retroviruses 9(11):1079–1086, 1993). Some insight into this soluble HIV-1 inhibitory activity has recently been gained by the observation that a cocktail of CC chemokines, RANTES, MIP-1α and MIP-1β (released by HTLV-I transformed CD8+ cells) effectively block replication of HIV in CD4+ lymphocytes (Cocchi et al., Science 270:1811–1815, 1995). These chemokines are naturally made by a number of immune cells including CD8+ cells. This inhibitory activity was observed against macrophage (M) tropic strains of virus but not against T-lymphocyte (T) tropic laboratory adapted strains of HIV (i.e., the laboratory adapted strain HIV IIIB). The simultaneous discovery of the HIV-1 inhibitory effects of chemokines and the isolation of fusin (or CXCR4) as a co-receptor for T-tropic strains of HIV-1 (Feng et al., Science 272:872–877, 1996) led to the discovery of a series of chemokine receptors that can act as co-receptors for entry of certain strains of HIV-1 into susceptible cells (Deng et al., Nature 381:661–666, 1996; Dragic et al., Nature 381:667–673,; Doranz et al., Cell 85:1149–1158, 1996; Marcon et al., J. Virol. 71:2522–2527, 1997; Chen et al., J. Virol. 71:2705–2714, 1997).

The mechanism of HIV-1 inhibition by the cocktail, RANTES, MIP-1α and MIP-1β is via the recently described second HIV-1 co-receptor, CCR-5, which is a ligand for each of these inhibitory chemokines. CCR-5 is a receptor for entry of M-tropic isolates into T-cells but not for entry of T-cell tropic strains (Deng et al., Nature 381:661–666, 1996; Dragic et al., Nature 381:667–673, 1996). The latter strains utilize the CXC chemokine receptor, CXCR4 or fusin and infection can be blocked with the ligand for CXCR4, SDF-1 (Oberlin et al., Nature 382:833–835, 1996). Additional members of the chemokine receptor family can be utilized by strains of HIV-1 and the related viruses HIV-2 and SIV to gain entry into cells (Doranz et al., Cell 85:1149–1158, 1996; Marcon et al., J. Virol. 71:2522–2527, 1997; Chen et al., J. Virol. 71:2705–2714, 1997; Liao et al., J.Exp.Med. 185:2015–2023, 1997). Two new members of the chemokine seven-transmembrane G-protein-coupled receptor family have recently been identified by expression cloning utilizing the SIV envelope protein. These receptors (Bob and Bonzo), expressed in lymphoid tissue, can be used by SIV as well as strains of HIV-2 and M-tropic HIV-1. The natural ligands for these receptors have yet to be identified (Deng et al., Nature 388:296–300, 1997). Early work on soluble CD8+ factors suggested that the CC class of chemokines may not be the only potent inhibitors released from CD8+ cells. The inhibitory activity found in CD8+ supernatants appeared to be against a broader range of HIV-1 isolates including both M-tropic and T-tropic viruses and appeared to at least in part inhibit HIV-1 transcription (Mackewicz et al., Proc. Natl. Acad. Sci. USA 92:2308–2312, 1995; Chen et al., AIDS Res. Human Retroviruses 9(11):1079–1086, 1993; Moriuchi et al., Proc. Natl. Acad. Sci. USA 93:15341–15345, 1996; Paliard et al., AIDS 10:1317–1321, 1996). In contrast, the chemokine cocktail of RANTES, MIP-1α and MIP-1β is believed to work primarily at the point of viral entry in the cell and is effective only against M-tropic strains of HIV-1. Additional inhibitory factors recently described include the HHV-8 chemokine homologue, vMipII, and macrophage-derived chemokine (MDC). vMipII acts like a receptor antagonist with binding to both CC as well as CXC chemokine receptors including CCR3, CCR5 and CXCR4 and, as predicted, has broad antiviral activity (Kiedal et al., Science 277:1656–1659, 1997). MDC was isolated from HTLV-I immortalized CD8+ cell lines. Predominantly made in activated PBMC (macrophages as well as CD8+ cells), this factor has broad activity against T-tropic and M-tropic strains. While MDC inhibits entry into macrophages and T-cells, it has no effect against the same strains in the transformed T-cell line, PM-1. Native MDC has inhibitory activity in the nanogram (ng) to microgram ($\mu$g) range (Pal et al., Science 278:695–698, 1997). Studies have demonstrated that CD8+-derived HIV-1 inhibitory activity from either primary or transformed cells is not blocked by neutralizing antibodies against β-chemokines and is not related to differences in MIP-1α, MIP-1β and RANTES levels (Moriuchi et al., Proc. Natl. Acad. Sci. USA 93:15341–15345, 1996; Paliard et al., AIDS 10:1317–1321, 1996). Therefore, CD8+ cells appear to make a number of natural HIV-1 inhibitory factors and further characterization of these factors should not only provide leads into new classes of inhibitory drugs against HIV-1 but will provide further understanding of host factors that might be play a role in controlling replication in certain individuals. This is best exemplified by the discovery of the inhibitory chemokines described above and the co-receptor CCR5. It has subsequently been determined that T-cells of certain individuals containing deletion mutations ($\Delta$32) in both alleles of the CCR5 receptor are highly resistant to infection in vitro with M-tropic strains of HIV-1 (Lin et al., Cell 86:367–377, 1996). In large population studies of HIV-1 infected individuals, carriers of this double deletion are extremely rare while the rates in other populations are 1% (Dean et al., Science 273:1856–1862, 1996). Individuals who are heterozygous for this deletion appear to become infected but have a somewhat slower progression to disease (Huang et al., Nature Med. 2:1240–1243, 1996). Furthermore, mutations in another co-receptor, CCR2b, while affording no protection from infection, confer some protection from disease progression (Smith et al., Science 277:959–965, 1997). Thus, further characterization of natural inhibitors has clearly impacted the field in both the area of understanding host factors that play a role in infection and progression as well as leading the way to a whole new class of inhibitors based on the chemokine/co-receptor interaction. The present invention is based on the discovery of novel natural inhibitors of HIV-1 replication isolated from CD8+ cells.

SUMMARY OF THE INVENTION

The present invention is directed to novel inhibitors of HIV replication which are capable of reducing, eliminating or preventing HIV infection and which are isolated from CD8+ lymphocytes. The invention is also directed to CD8+ cell lines which secrete these novel inhibitors. The invention is further directed to compositions comprising an inhibitor of the invention and to methods for the use of such compositions in the prevention and/or treatment of HIV infection.

BRIEF DESCRIPTION OF THE DRAWINGS

FIG. 2. Comparison of inhibition profiles of CD8+ cell lines established from HIV-infected patients.

DETAILED DESCRIPTION OF THE INVENTION

Figure 1:
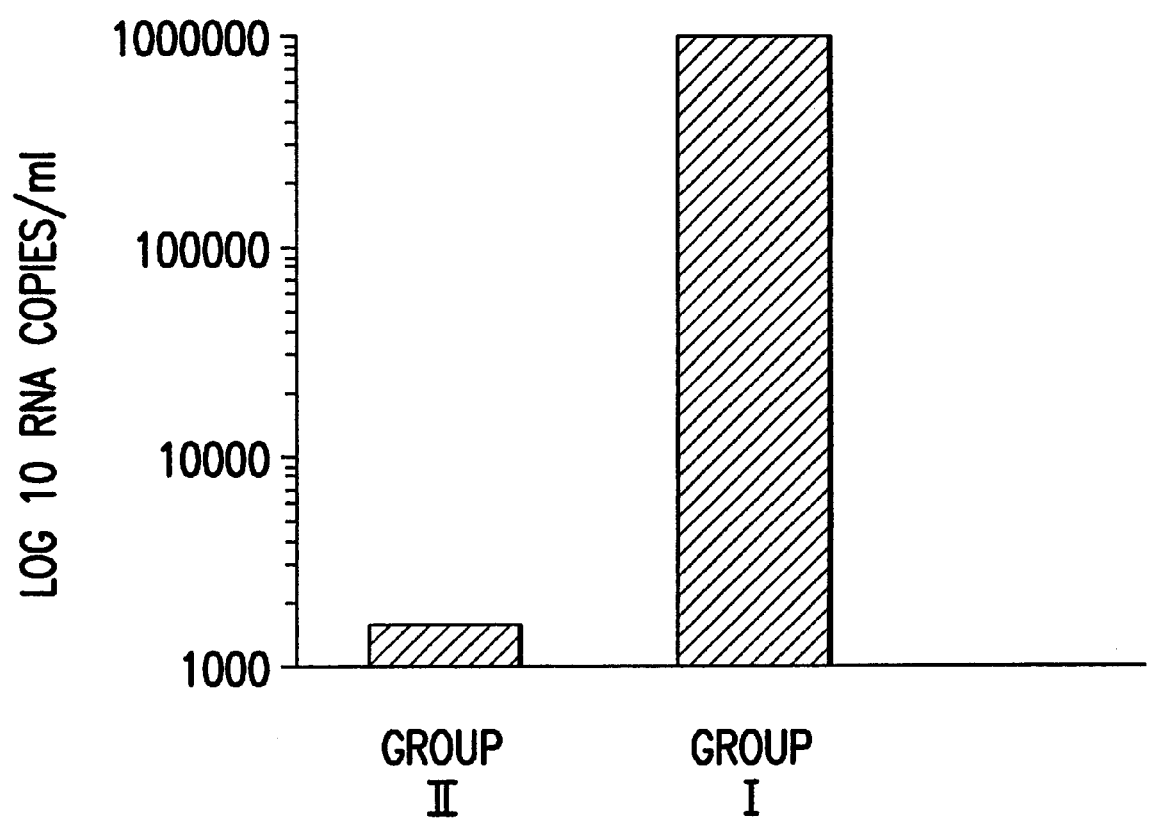
FIG. 1. Viral RNA levels in patient cohorts.

The present invention is directed to novel inhibitors of HIV replication which are capable of reducing, eliminating or preventing HIV infection and which are isolated from CD8+ lymphocytes. The invention is also directed to cell lines which secrete these novel inhibitors. The invention is further directed to compositions comprising an inhibitor of the invention and to methods for the use of such compositions in the prevention and/or treatment of HIV infection.

An inhibitor of the invention is defined as a peptide or polypeptide secreted by CD8+ cells which is capable of reducing, eliminating or preventing infection by HIV or other retroviruses. The invention is also directed to nucleic acids encoding such inhibitors, and to nucleic acids which hybridize to a known coding sequence at high stringency and encode an inhibitor of the invention. The invention further encompasses analogs, homologs, derivatives and truncated fragments of an inhibitor of the invention which retain these defined functional properties.

As used herein, the term "peptide" refers to an oligomer of at least two contiguous amino acids, linked together by a peptide bond, and not greater than fifty amino acids. As used herein, the term "polypeptide" refers to an oligomer of at least fifty amino acids.

As used herein, "substantially corresponds" means an amino acid sequence having approximately 70% homology in amino acid sequence to an inhibitor of the invention. For example, conservative amino acid substitutions which do not alter the chemical type of amino acid residue in an inhibitor can be introduced into the inhibitor provided that its functional activity is retained. By "homolog" is meant the corresponding peptides or polypeptides which are derived from an inhibitor of the invention so long as the functional properties of the inhibitor are retained.

By "analog" is meant substitutions, rearrangements, deletions, truncations and additions to the amino acid sequence of an inhibitor, so long as its functional properties are retained. Analogs also include inhibitors which contain additional amino acids added to either end of the peptides that do not affect biological activity, e.g., the presence of inert sequences added to a functional inhibitor which are added to prevent degradation. An algorithm can be used in the identification of homologs and analogs, such as the BLASTP program (Altschul, J.Mol.Evol. 36:290, 1993; Altschul, J.Mol.Biol. 215:403, 1990). In a preferred embodiment, a preferred length for a truncated, functional derivative of an inhibitor of the invention ranges from 4 amino acids to 35 amino acids.

The criticality of particular amino acid residues in an inhibitor may be tested by altering or replacing the residue of interest. For example, the requirement for a cysteine residue, which can be involved in the formation of intramolecular or intermolecular disulfide bonds, can be tested by mutagenesis of the cysteine to another amino acid, for example, tyrosine, which cannot form such a bond.

Inhibitors of the invention are described with reference to the following amino acid nomenclature wherein A=Ala=Alanine
R=Arg=Arginine
N=Asn=Asparagine
D=Asp=Aspartic acid
B=Asx=Asparagine or aspartic acid
C=Cys=Cysteine
Q=Gln=Glutamine
E=Glu=Glutamic acid
Z=Glx=Glutamine or glutamic acid
G=Gly=Glycine
H=His=Histidine
I=Ile=Isoleucine
L=Leu=Leucine
K=Lys=Lysine
M=Met=Methionine
F=Phe=Phenylalanine
P=Pro=Proline
S=Ser=Serine
T=Thr=Threonine
W=Trp=Tryptophan
Y=Tyr=Tyrosine
V=Val=Valine.

In preferred embodiments, an inhibitor of the invention comprises a polypeptide having an amino acid sequence subtantially corresponding to one of the following sequences as listed:

EQVEASVAS (SEQ. ID NO. 1)
EQVEASVASVRSLY (SEQ. ID NO. 2)

Chimeric inhibitors which combine one or more of the preferred peptides or polypeptides or segments or fragments thereof are within the scope of the invention. Inhibitors of the present invention also include cyclic or derivatized peptides, and further include peptides containing D-amino acids as well as L-amino acids.

The peptide and polypeptide inhibitors of the invention can be synthesized according to Merrifield solid-phase synthesis techniques (Kotler et al., Proc. Natl. Acad. Sci. 85:4185–4189, 1985; Barany et al., in Gross et al., eds., *The Peptides*, Vol. 2, Academic Press, 1980) or other techniques of peptide synthesis known to those skilled in the art. After cleavage and deprotection, synthetic peptides or polypeptides can be purified by, for example, gel filtration, chromatography, and any reverse-phase column/HPLC system known to those skilled in the art. Peptide inhibitors derived from an inhibitor of the invention may also be produced by chemical or enzymatic digestion of the full-length protein using techniques that are known to those skilled in the art.

Peptides and polypeptides may also be prepared by standard recombinant DNA technology using techniques well known to those skilled in the art for nucleotide-based based peptide design (Sambrook et al., *Molecular Cloning: A Laboratory Manual*, 2nd edition, Cold Spring Harbor Press, Cold Spring Harbor, N.Y., 1989; Ausubel et al., *Current Protocols in Molecular Biology*, John Wiley and Sons, New York, 1995). Site-directed mutagenesis using recombinant DNA techniques, for example, may be used to prepare peptide analogs and homologs from parent peptides.

An inhibitor may be recovered by purification from a cell line secreting such an inhibitor, using standard techniques for protein purification which are known to those skilled in the art, including, but not limited to, size fractionation, ion-exchange chomatography, and reverse-phase chromatography.

The amino acid sequences of the peptides and polypeptides can be confirmed and identified by amino acid composition analysis as well as manual and automated Edman degradation and determination of each amino acid, HPLC analysis, or mass spectrometry.

The inhibitors of the invention are isolated from CD8+ cells which can be isolated from uninfected or HIV-infected individuals. Such cells can be prepared by isolating monocytes from peripheral blood mononuclear cells (PBMC) using ficoll-hypague purification. Preferably, such cells are then immortalized using *Herpesvirus saimiri*, and the surviving cells are purified by limiting dilution and analyzed by fluorescent-activated cell sorting (FACS). Isolation of soluble inhibitors is accomplished by recovering supernatant from cells of interest and using cell-free supernatants in assays to determine the presence of an inhibitor.

Partial amino acid sequences corresponding to an inhibitor molecule isolated from CD8+ cells can be used to isolate a full-length nucleotide sequence encoding the inhibitor using standard techniques of molecular biology known to those skilled in the art. For example, degenerate nucleotide primers can be generated from a known amino acid sequence identified through purification of a cell supernatant which exhibits the property of inihibiting the replication of HIV. Such primers can then be used in reverse-transcription-polymerase chain reaction (RT-PCR) of RNA isolated from active cell lines exhibiting the desired antiviral characteristics. An RNA molecule which is amplified using these primers can be used to probe a Northern blot of RNA from the original cell line from which the amino acid sequence has been isolated in order to identify an mRNA which corresponds to an inhibitory polypeptide.

Alternatively, a partial amino acid sequence corresponding to an inhibitor can be used to generate immunological reagents. A synthetic peptide which corresponds to the identified sequence can be conjugated to keyhole limpet hemocyanin (KLH) and used to immunize animals of interest such as rabbits and/or mice. Polyclonal antisera can be generated and monoclonal antibodies can be derived using standard techniques. These reagants can be used with an expression library generated from a cDNA library obtained from a cell line of interest which exhibits the requisite antiviral properties in order to identify an inhibitory polypeptide. A commercially available vector which allows library construction for expression cloning with an antibody or for screenning with a DNA probe can be used in these protocols, such as the vector Lambda TriplEX (Clontech, Palo Alto, Calif.). Large scale purification of an inibitory polypeptide can be accomplished by cloning a cDNA into a bacterial expression vector, such as the pTrcHis A,B,C vector (Invitrogen, San Diego, Calif.), which allow high-level expression and ready purification according to the manufacturer's protocol.

The inhibitors of the invention are characterized by an ability to decrease or prevent viral replication in an active HIV infection in vivo or in a cellular model system. An inhibitor may also be characterized by its effects in altering, reducing or eliminating viral morphogenesis, replication, or virion infectivity. Where an inhibitor is incubated with HIV-infected cells, the production of infectious virus progeny is determined relative to control experiments without inhibitor.

Inhibitors can be characterized in tissue culture models of viral infection using cells infected with any lentiviral or retroviral infection, including, but not limited to, those resulting from HIV-1, HIV-2, simian immunodeficiency virus (SIV), feline immunodeficiency virus (FIV), bovine immunodeficiency virus (BIV), visna virus and all strains and isolates thereof. Specific HIV strains which have tropism for certain cell types can be used, including the macrophage-tropic HIV Ba-1, and the T-tropic HIV IIIB and MN. In general, isolates can include lymphotropic and macrophage-tropic strains, primary strains derived from blood cells or tissues, and North American, European, African and Asian isolates.

Primary cells or cell lines which can be used for inhibitor studies on virus-infected cells are preferably those that are susceptible to such viral infection. Such cells include, for example, peripheral blood lymphocytes (PBL), especially CD4+ cells, and macrophages.

Assay systems which employ a vector-delivered full or partial HIV genome into a eucaryotic cell can be used to simulate the production of viral proteins and virion production, and such cells can be used in the characterization of an HIV inhibitor.

To assess whether an inhibitor reduces or eliminates the generation of infectious viral progeny, the quantity and type of infectious progeny are assayed at suitable times post-infection. Evidence of microscopically observed viral spread, cytopathic effect, and increased amounts of the p24 capsid protein can provide an assessment as to whether infectious progeny are being generated. The assessment of progeny virus infectivity may be determined further by recovery of infected cells and co-cultivation with suitable cells (e.g., PBL or macrophages) or by the recovery of supernatant from the infected cells and cell-free infection of suitable cells. Another method of phenotypic determination involves the observation of progeny virus for morphological analysis, e.g., by electron microscopy.

Quantitative assessment of an HIV infection conducted in the presence of an inhibitor can also be determined using molecular markers, for example, by assaying viral p24 production by ELISA assay, reverse transcriptase activity, or viral DNA synthesis by quantitative PCR using standard techniques known to those skilled in the art.

A DNA encoding an inhibitor can be used to engineer cell lines which constitutively express the inhibitor in order to test the effect of an inhibitor on different isolates of HIV-1 or other HIV strains. Such isolates include lymphotropic and macrophage-tropic strains, primary strains derived from blood cells or tissues, and North American, European, African and Asian isolates. Such methods can allow the selection of an inhibitor which has optimal inhibitory effect on a particular viral isolate of interest.

The inhibitors of the invention can be tested in animal models of HIV infection, including the SCID-Hu mouse model of HIV-1 infection (Aldrovandi et al., J. Virol. 70:1505, 1996) and SIV-infected monkeys. Such models of infection are suitable for testing the inhibitors of the invention for efficacy against challenge with HIV or other lentiviruses and other retroviruses in order to identify those inhibitors which can be used for prevention or treatment of viral infection.

The inhibitors of the invention can be assayed to determine the concentration required to achieve an antiviral effect against a target virus. A convenient variable for measurement is the concentration of an inhibitor required to inhibit 50% of viral replication ($IC_{50}$), whether assayed in cell culture or with the use of a molecular marker such as the measurement of viral p24 production by ELISA assay, presence of viral RNA, reverse transcriptase activity, or viral DNA synthesis by quantitative PCR using standard techniques known to those skilled in the art.

Inhibitors of the invention can be evaluated for cytotoxic effects using standard assays that measure cell viability. Such assays include $^{14}C$ protein hydrolysate, $^{3}H$ thymidine uptake, MTT reduction, and cell growth. Such parameters as $TD_{50}$ (toxic dose to 50% of the tested culture) can be derived from such assays. Comparison of the $TD_{50}$ so derived with the $IC_{50}$ (inhibitor concentration required to inhibit 50% of the viral marker being tested or viral replication) can indicate a therapeutic index for a particular compound (TI). Preferably, the $IC_{50}$ is at least ten times higher than the $TD_{50}$, and the $IC_{50}$ is effective at a minimum of $10^{-6}M$ in culture to be considered as a prospective inhibitor of the invention. Most preferably, an inhibitor of the invention exhibits an $IC_{50}$ of $10^{-7}M$ or $10^{-8}M$.

The inhibitors of the invention are useful in the isolation of HIV or other lentiviral and retroviral mutants which are resistant to the inhibitor but which can be used in subsequent screens to identify other antiviral agents to which they are susceptible, thereby generate a profile of inhibition for a particular viral isolate.

In preferred embodiments of the invention, an inhibitor of HIV replication comprises a polypeptide defined by the following properties: a) isolated from the CD8+ cell line K#1 50K; b) inhibits the replication of HIV Ba-1 in macrophages and the replication of HIV IIIB in CD4+ cells; c) is not a cytokine selected from the group consisting of RANTES, MIP-1α and MIP 1-β; d) a molecular weight of approximately 8 kd; e) inhibits the replication of HIV in the viral life cycle following reverse transcription but before integration into the cellular genome; f) is stable at pH 2; g) maintains activity after being subjected to freezing and thawing; and h) comprises a peptide or polypeptide having an amino acid sequence which substantially corresponds to SEQ. ID NO. 1 or SEQ. ID NO. 2.

In other preferred embodiments of the invention, an inhibitor of HIV replication comprises a polypeptide defined by the following properties: a) isolated from the CD8+ cell line K#1 50K; b) inhibits the replication of HIV Ba-1 in macrophages and the replication of HIV IIIB in CD4+ cells; c) is not a cytokine selected from the group consisting of RANTES, MIP-1α and MIP 1-β; d) a molecular weight of approximately 8 kd; e) inhibits the replication of HIV in the viral life cycle following reverse transcription but before integration into the cellular genome; f) is stable at pH 2; and g) maintains activity after being subjected to freezing and thawing.

The invention is further directed to CD8+ cell lines which are the source of one or more of the soluble factors of the invention which are capable of inhibiting the replication of HIV. CD8+ cells can be recovered from uninfected or HIV-infected individuals. Cells of interest can be transformed by *Herpesvirus saimiri* (HVS) in order to establish cell lines for further study or to be used as continuing sources of inhibitory factors (Weber et al., Proc. Natl. Acad. Sci. USA 90:11049–11053, 1993; Biesinger et al., Proc. Natl. Acad. Sci. USA 89:3116–3119, 1992). In preferred embodiments, the cell lines of the invention include the CD8+-derived cell lines K#1 50K, and Caf 10. The invention is also directed to any single cell clones which are derived from the cell lines of the invention.

In view of the above noted properties of the inhibitors of the invention, it is further contemplated that the inhibitors of the invention may be used in compositions for the prevention or treatment of an HIV or other lentiviral and retroviral infections, and the treatment of consequent pathologic conditions such as AIDS. Another aspect of the invention, therefore, is directed to methods for preventing and treating an HIV or other lentiviral or retroviral infection by administering a composition containing one or more of the inhibitors of the invention to an individual infected with or exposed to HIV for a time and under conditions to accomplish such result.

The inhibitors, compositions and methods of the invention can be used in the treatment of HIV-positive individuals, including those exhibiting the conditions of AIDS-related complex (ARC) and AIDS, as well as those who are asymptomatic. These inhibitors, compositions and methods can also be used in the prophylaxis of HIV or other lentiviral and retroviral infections, and can also be used the treatment or prophylaxis of veterinary infections caused by lentiviruses and other retroviruses.

The inhibitors of the invention may be used alone or in combination with other known or to be discovered inhibitors of HIV replication, including, but not limited to, other antiviral compounds, immunomodulators, antibiotics, vaccines, chemokines and other therapeutic agents. Particular agents which can be used in combination with the inhibitors of the invention include, but are not limited to, azidothymidine (AZT), dideoxyinosine (DDI), dideoxycytosine (DDC), saquinavir, indinavir, ritonavir, and other antiviral compounds. The inhibitors of the invention may also be used in combination with agents which are used to treat secondary complications of HIV infection, e.g., gancyclovir used in the treatment of cytomegalovirus retinitis. Combination therapy may retard the development of drug-resistant mutants by requiring multiple mutation events for the emergence of a fully drug-resistant isolate.

The inhibitors of the present invention may be administered to a host as a composition in an amount effective to inhibit HIV infection and/or replication in target cells. The compositions contain an effective dosage of at least one of the inhibitors of the present invention, together with an acceptable carrier.

The inhibitors of the invention may be systematically administered for preventing or treating an HIV or other lentiviral or retroviral infection. When used systemically, the inhibitor compositions may be formulated as liquids, pills, tablets, lozenges or the like, for enteral administration, or in liquid form for parenteral injection. The peptides and/or polypeptides (or inhibitor-protein conjugates) may be combined with other ingredients such as carriers and/or adjuvants. There are no limitations on the nature of such other ingredients, except that they must be physiologically acceptable, efficacious for their intended administration and cannot degrade the activity of the active ingredients of the compositions. An inhibitor can also be covalently attached to a protein carrier, such as albumin, so as to minimize diffusion of the inhibitor.

As used herein, a physiologically acceptable carrier includes any and all solvents, dispersion media, coatings, antibacterial and antifungal agents, isotonic agents and the like. The use of such media and agents are well-known in the art.

The forms of the compositions suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyol such as glycerol, propylene glycol, polyethylene glycol, suitable mixtures thereof, surfactants or vegetable oils. Sterilization can be accomplished by an art-recognized technique, including but not limited to, filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing the subject inhibitors is accomplished by incorporating these compounds in the required amount in the appropriate solvent with various ingredients enumerated above, as required, followed by sterilization, preferably filter sterilization. To obtain a sterile powder, the above solutions are vacuum-dried or freeze-dried as necessary.

The polypeptide compositions also may be impregnated into transdermal patches, plasters and bandages, preferably in a liquid or semi-liquid form.

When the inhibitors of the invention are administered orally, the compositions thereof containing an effective dosage of the peptide may also contain an inert diluent, an assimilable edible carrier and the like, be in hard or soft shell gelatin capsules, be compressed into tablets, or may be in an elixir, suspension, syrup or the like.

The subject inhibitors are thus compounded for convenient and effective administration in physiologically effective amounts with a suitable pharmaceutically acceptable carrier in a therapeutically effective dosage.

The precise effective amount of inhibitor to be used in the methods of this invention to prevent or treat an HIV infection cannot be stated because of the nature of the infectious process. It must be noted that the amount of inhibitor to be administered will vary with the degree of infection in an individual, as determined by such parameters as viral load and CD4 cell counts. Individual-specific variables such as age, weight, general health, gender, diet, and intake of other pharmaceuticals can factor into the choice of dosage. The design of an optimal protocol for an infected individual may further consider the identity of the viral isolate(s) isolated from an infected individual with an infection for optimal result. A further consideration in protocol design would be the presence of a viral strain which is already resistant to existing protease or reverse transcriptatse inhibitors.

The amount of an inhibitor of the invention per unit volume of composition for administration depends upon the amount of active ingredients that are afforded directly to the site of infection. However, it can generally be stated that a peptide or polypeptide inhibitor of the invention should preferably be present in an amount of at least about 1.0 nanogram per milliliter of combined composition, more preferably in an amount up to about 1.0 milligram per milliliter.

Systemic dosages depend on the age, weight and condition of the individual and on the administration route. For example, a suitable dosage for the administration to adult humans ranges from about 0.01 to about 100 mg per kilogram body weight. The preferred dosage ranges from about 0.5 to about 5.0 mg per kilogram body weight.

Since the inhibitory compositions of this invention are effective in reducing or eliminating the ability of HIV or other lentiviruses and other retroviruses to generate infectious progeny, periodic readministration of the compositions may be indicated and preferred.

The peptide and polypeptide inhibitors of the invention can also be delivered to an individual by administering a vector that comprises and expresses a nucleic acid encoding the inhibitor. DNAs encoding one or more of the inhibitors of the invention can be delivered to the cells of an individual in need of such an inhibitor by any method of gene transfer known to those skilled in the art, including, but not limited to, viral vectors, lipid-mediated delivery, transfection, electroporation, as well as other methods. Viral vectors which can be used to deliver such inhibitors include those derived from DNA and RNA viruses, including, but not limited to, adenovirus, herpesvirus, poxvirus, retrovirus, and adeno-associated virus.

Parameters, which are used to monitor the effect of an inhibitor of the invention administered to an individual with an established HIV infection or administered to an individual for prophylaxis, include the use of CD4 counts, plasma viral RNA concentration, viral phenotype, p24 antigen concentration, viral phenotype, level of anti-HIV antibodies as well as other markers of the clinical progression of an HIV infection known to those skilled in the art.

It will be recognized that the inhibitors and methods of the invention can be used in the treatment or prevention of any other lentiviral or retroviral infection, including, but not limited to, those resulting from HIV-1, HIV-2, simian immunodeficiency virus (SIV), feline immunodeficiency virus (FIV), bovine immunodeficiency virus (BIV), visna virus and all strains and isolates thereof.

The practice of the invention employs, unless otherwise indicated, conventional techniques of protein chemistry, molecular virology, microbiology, recombinant DNA technology, and pharmacology, which are within the skill of the art. Such techniques are explained fully in the literature. See, e.g, *Current Protocols in Molecular Biology,* Ausubel et al., eds., John Wiley & Sons, Inc., New York, 1995; *Remington's Pharmaceutical Sciences,* 17th ed., Mack Publishing Co., Easton, Pa., 1985; and *Molecular Cloning: A Laboratory Manual,* Sambrook et al., eds., 2nd edition, Cold Spring Harbor Press, Cold Spring Harbor, N.Y., 1989.

The following examples further illustrate the invention.

EXAMPLE 1

Patient Cohort Used For HIV Studies

As part of studies to determine correlates of disease progression in HIV-infected children, cohorts of patients with differing disease progression were identified. Group I consisted of five children with rapidly progressive disease having AIDS-related symptoms within two years of infection; group II were long-term survivors who have remained asymptomatic for at least 8 years following infection and have CD4+ counts of >500/mm3. Plasma RNA levels were determined using the Amplicor assay (Roche Molecular Diagnostics). Plasma viral RNA levels were significantly lower (p<0.05) in group II compared to the rapid progressors with two of the group II survivors having no detectable plasma RNA intermittently (FIG. 1). Since these children represent the extreme spectrum of disease progression, these two populations have been the focus of studies to identify host and viral factors that might contribute to disease progression.

EXAMPLE 2

Establishment Of CD8+ Cell Lines

Attempts to isolate HIV-1-inhibitory cell factors have been limited by the number of primary cells available and by the limited life span of these cells in tissue culture. Prior to initiating attempts to isolate these host factors, primary immune cells from HIV-infected children were transformed in order to have an unlimited supply of these cells for tissue culture studies and protein isolation. *Herpesvirus saimiri* (HVS) was the preferred virus for transforming these primary cells, because work by several groups has demonstrated that primary cells transformed with this virus retain many of the properties of the original primary cells in contrast to cells transformed with other virus. HVS-transformed cells require IL-2 for continuous growth, retain their original T-cell receptor expression and specific antigen recognition after prolonged in vitro growth (Weber et al., Proc. Natl. Acad. Sci. USA 90:11049–11053, 1993; Biesinger et al., Proc. Natl. Acad. Sci. USA 89:3116–3119, 1992). Therefore, lymphocytes were isolated from PBMCs from children in each study cohort along with normal donor PBMCs by ficoll-hypague purification and cells were infected with HVS strain C-488. After 4 weeks in culture with conditioned medium and IL-2, surviving cells were purified by limiting dilution and analyzed by FACS. Both CD4+ and CD8+ cell lines were obtained and further characterized. Purified CD8+ cells were screened for soluble HIV-1 inhibitory activity in transformed and primary CD4+ cells and in primary macrophages utilizing both primary and laboratory-adapted strains of HIV-1. The CD4+ transformed cell line used for these studies was also transformed by HVS and was very broadly permissive for laboratory-adapted as well as primary HIV isolates.

EXAMPLE 3

Inhibitory Activity Of HVS-Transformed CD8+ Cell Lines

Cell-free supernatants from multiple CD8+ cell lines established from HIV-infected children were tested for HIV-1 inhibitory activity against HIV-1 Ba-1 (a macrophage tropic laboratory adapted strain), HIV IIIB (a T-tropic laboratory adapted strain), MN (a T-tropic laboratory adapted strain), and primary HIV-1 isolates. The primary viral isolates were obtained from patients, minimally passed in culture using allogeneic PBMCs and characterized for their ability to form syncytium in culture using the MT-2 assay. In each case, the CD4+ cell line or primary cells were incubated with virus for two hours, the cells washed and subsequently cultured in the presence of conditioned media (RPMI) with IL-2 and CD8+ cell supernatant (usually representing 25% of the culture media unless otherwise stated). HIV-1 replication was monitored by p24 (gag) protein production measured by ELISA (Dupont). As shown in FIG. 2, cell lines with inhibitory activity against HIV-1 IIIB and HIV-1 Ba-1 were isolated from HIV-infected children with rapid disease progression (closed symbols) as well as from HIV-infected children with long-term non-progression (open symbols). In this assay, inhibitory activity was tested in a broadly permissive HVS-transformed CD4+ cell line. The profile of inhibition was not identical against IIIB and Ba-1 suggesting that different cell lines synthesized different inhibitory factors. The anti-HIV activity of the cell line, Caf 10, was further characterized against a panel of isolates in the HVS-transformed cells. Caf 10 cell supernatant potently inhibited the replication of HIV-1 MN, HIV-1 Ba-1, HIV-1 IIIB and a primary isolate.

Figure 3:
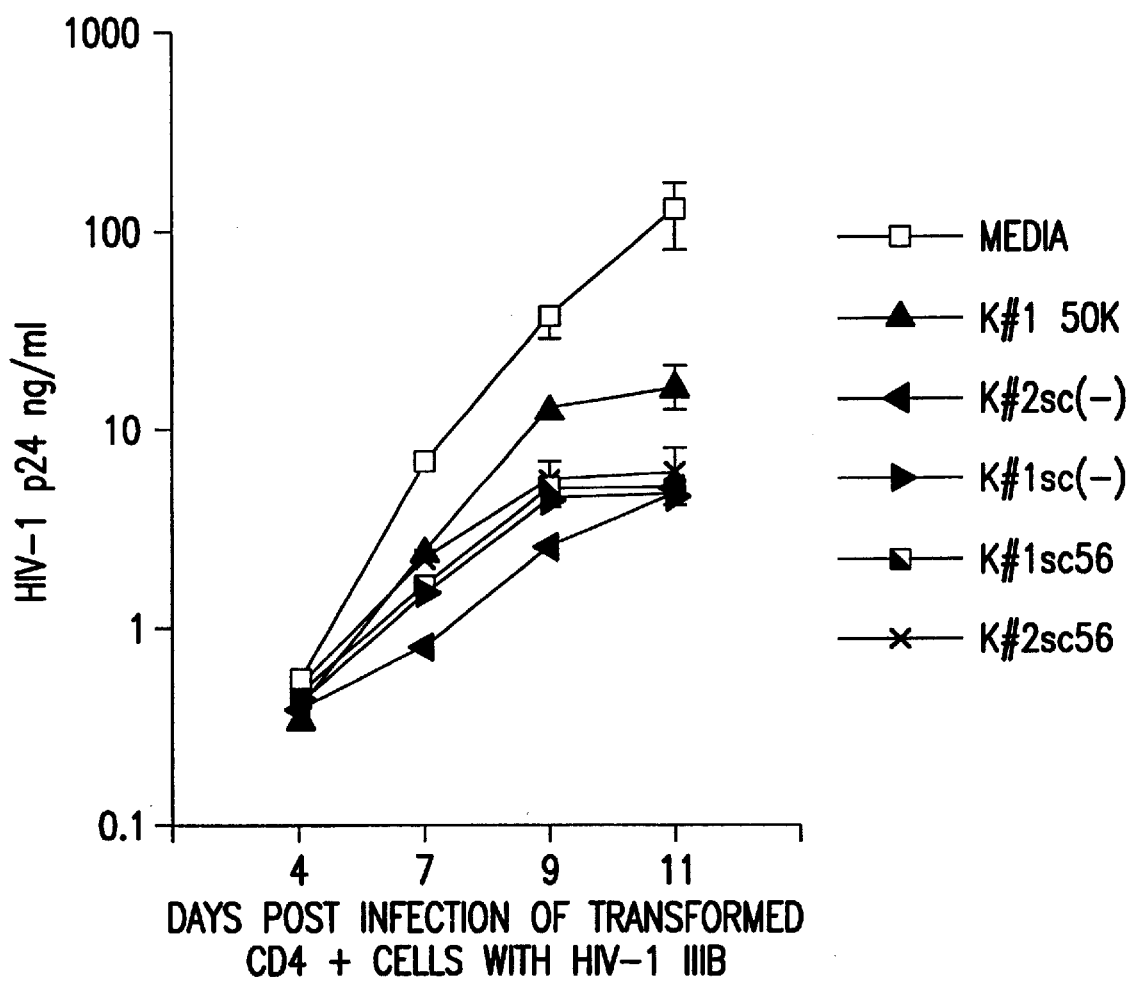
FIG. 3. Comparison of inhibition profiles of CD8+ cell lines established from healthy donors.
Figure 4B:
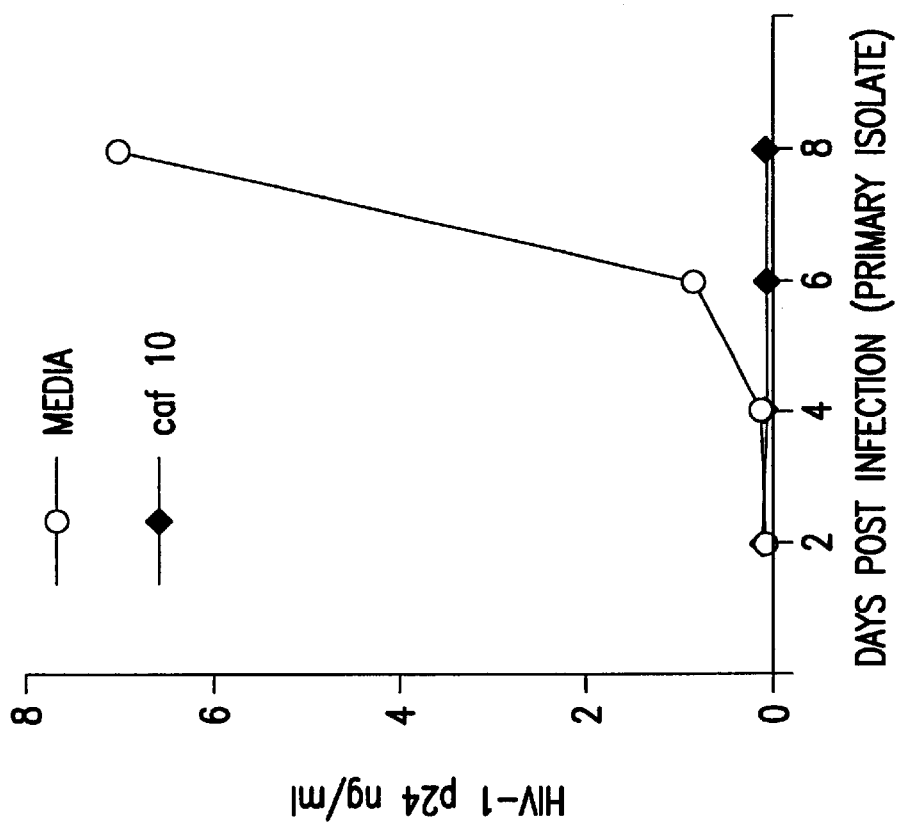
FIG. 4. Inhibition profiles of Caf 10 and K#1 50K cell lines.
Figure 4A:
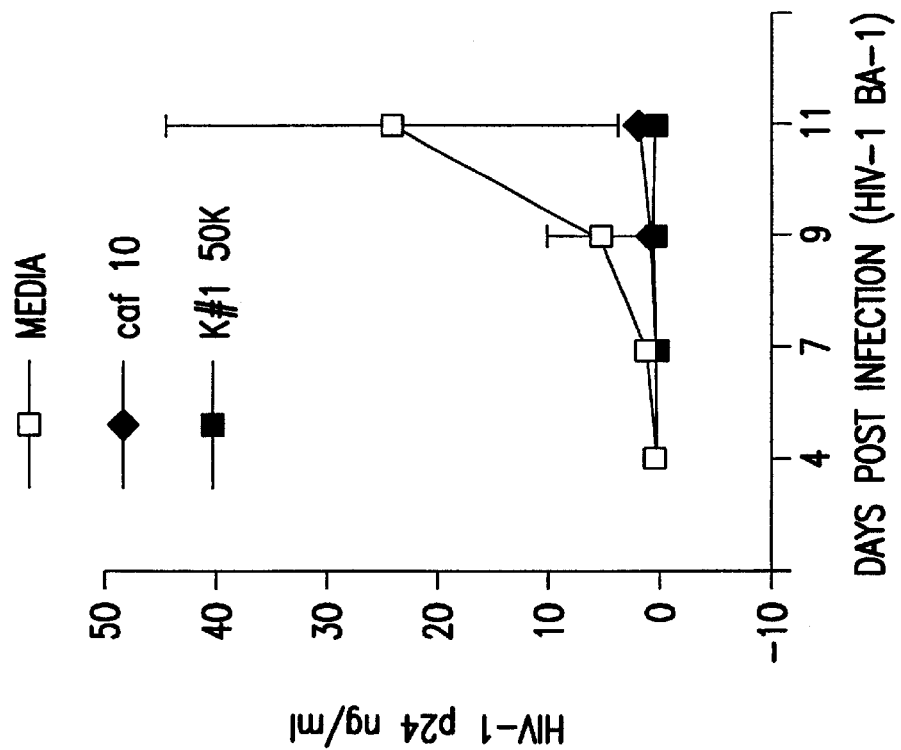
Figure 5A:
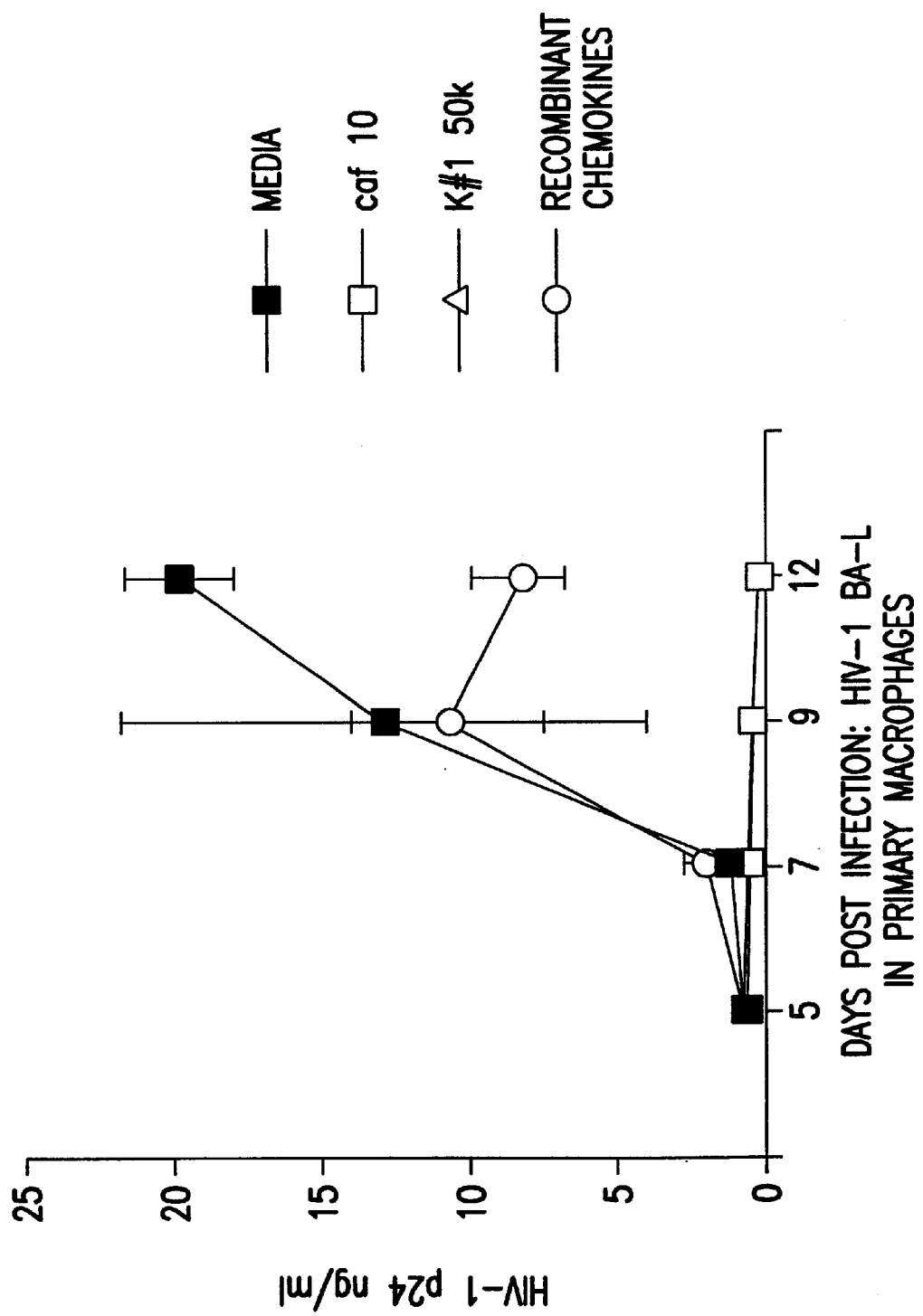
FIG. 5. Comparison of inhibition profiles of isolated CD8+ supernatants and known chemokines.
Figure 5B:
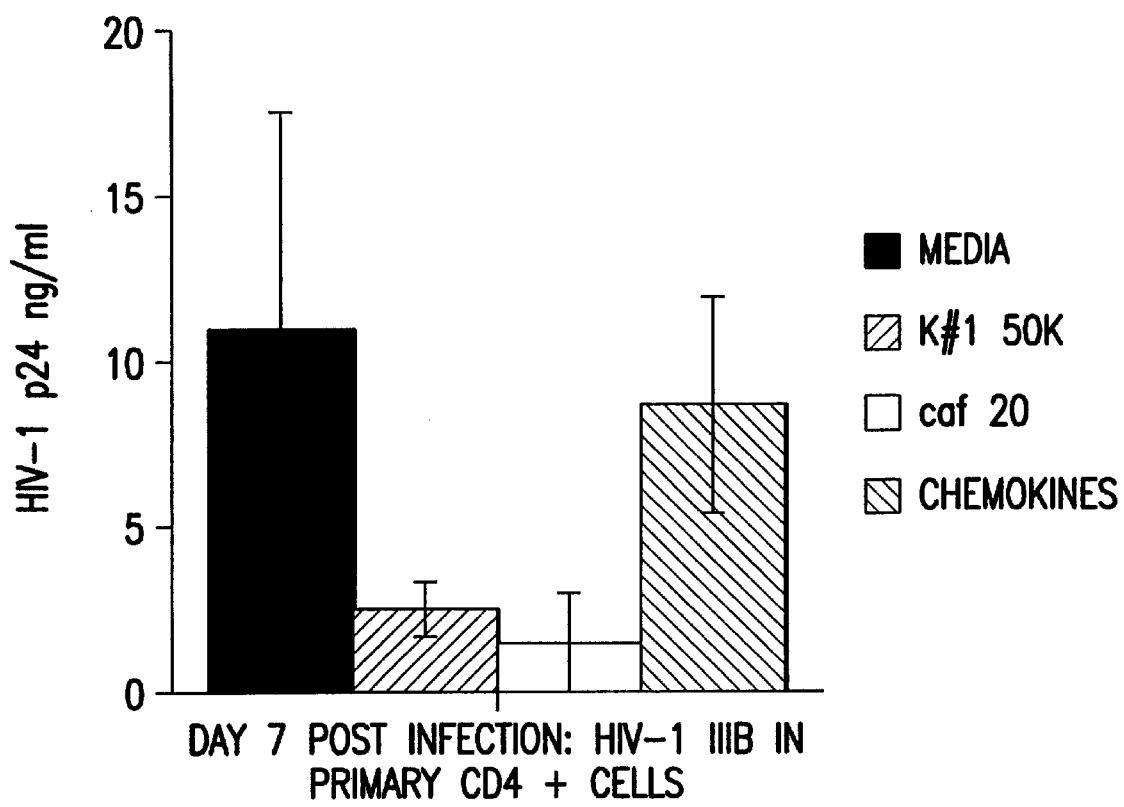

In subsequent experiments, several CD8+ cells lines with significant HIV-1 inhibitory activity were also isolated from a normal healthy donor as well (FIG. 3). Several inhibitory cell lines were established from this healthy donor. While the ability to demonstrate HIV-1 inhibitory activity appeared to be independent of the state of HIV-infection of the host, these cell lines exhibited potent, broad anti-viral activity and could be used for identification of these inhibitory factors. The apparent lack of correlation between production of these factors and the clinical status of the host is not surprising in that the resulting cell lines, after infection with HSV, are all highly activated and transformed and may not reflect the characteristics of the original cell in vivo. FACS analysis of the cell lines revealed an activated phenotype in all of the transformed lines with high expression of both CD25 as well as HLA-DR. Attempts to further activate the cells with phytohemagglutinin (PHA) or co-culture with irradiated allegeneic cells resulted in no significant enhancement of HIV-1 inhibitory activity. While all of the transformed cell lines were IL-2 dependent for growth, a number of the cell lines had slow doubling times even in the presence of IL-2. Many of the cell lines had doubling times>four days. However, two cell lines grew relatively well in culture, K#1 50K from the normal donor had a doubling time of 2 days and Caf 10, from a rapidly progressing, infected child had a doubling time of 3 days. These lines were further characterized for purification of the inhibitory factors. As shown in FIG. 4, supernatant from these two cell lines inhibited HIV-1 Ba-1 (on the left) and a primary viral isolate (on the right) grown in the HVS-transformed T-cell line. Supernatants from these cells also inhibited Ba-1 and IIIB growth in primary macrophages and primary CD4+ cells respectively. The activity against Ba-1 in macrophages and against IIIB in CD4+ cells was distinct from that of a cocktail of chemokines, as discussed below (FIG. 5).

Figure 6:
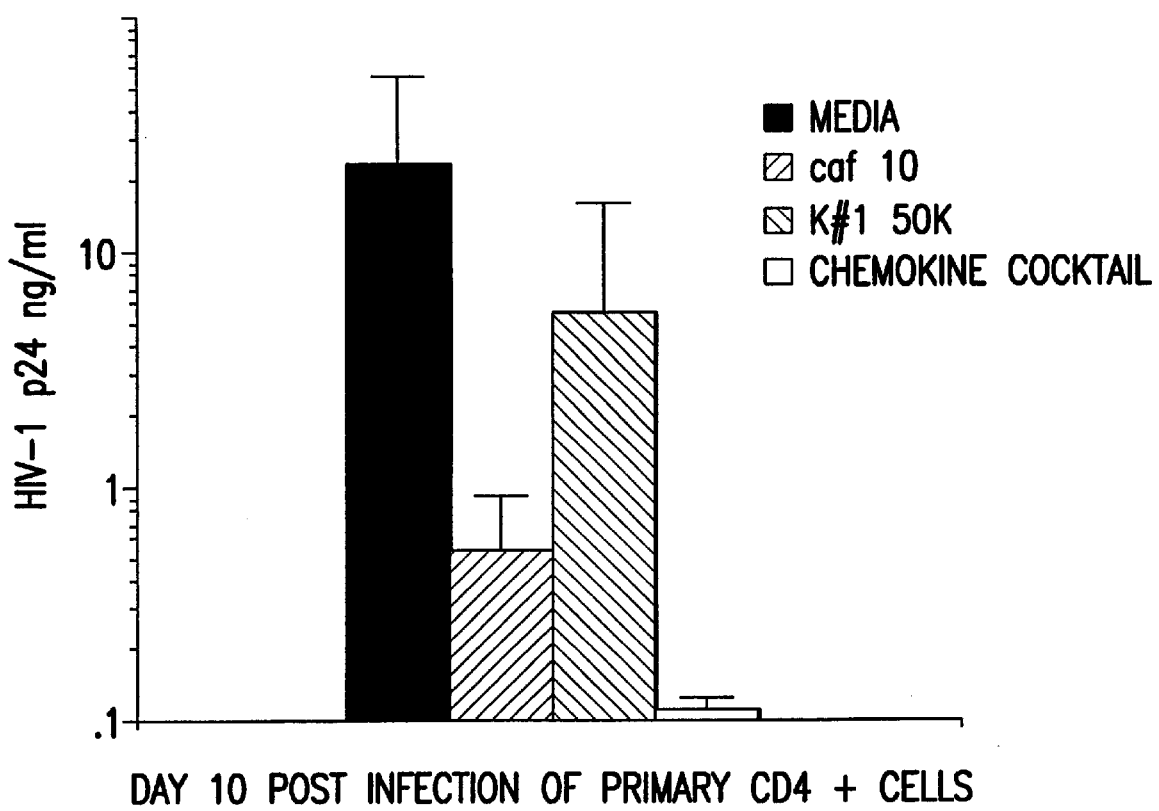
FIG. 6. Comparison of inhibition profiles of isolated CD8+ supernatants and known chemokines.

Activity was also assayed against primary isolates in primary CD4+ cells. As shown in FIG. 6, modest activity was seen against a primary NSI isolate in these cells and differed between the two cell lines. While Caf 10 activity was close to the activity displayed by the expected activity of the chemokine cocktail containing RANTES, MIP-1α and MIP-1β, K#1 50K was significantly less. Nevertheless, the latter cell line consistently inhibited Ba-1 infection of primary macrophages.

EXAMPLE 4

Inhibitory Activity Is Not Due To Know Chemokines

Several lines of evidence suggested that the inhibitory activity in these lines was distinct from the reported inhibitory effects of the chemokines cocktail RANTES, MIP-1α and MIP-1β. The activity against the T-tropic isolate IIIB was distinctly different from a cocktail of these chemokines, each present at a concentration of 200 ng/ml, which showed no activity (FIG. 5). HIV-1IIIB does not use the common receptor for these ligands, CCR5, but uses the alternative receptor, CXCR4, and therefore would not be expected to be inhibited by the chemokine cocktail (Feng et al., Science 272:872–877, 1996). Measured chemokine production from the Caf 10 and K#1 50K cell lines was variable and showed no correlation with activity as shown in Table 1 and FIG. 2.

TABLE 1

Chemokine Production by CD8+ Cell Lines

| Cell line | Rantes (ng/ml) | MIP-1α (ng/ml) |
|---|---|---|
| Caf l0 | 5.880 | 1.822 |
| K#1 50K | 2.433 | 2.615 |
| K#1 50K (serum-free) | 0.895 | 0.934 |
| nd 1 | 2.226 | |
| nd 2 | 2.210 | |
| wrsc#1 | 3.315 | 2.515 |

When the CD8+ inhibitory lines were grown in serum free media with RANTES and MIP-1α<1.0 ng, inhibitory activity against HIV-1 Ba-1 persisted and was equal to or greater than a full cocktail of the β-chemokines at 200 ng/ml. Upon subsequent purification of inhibitory activity (see below), fractions retaining the full inhibitory activity against Ba-1 contained no measurable RANTES or MIP-1α by Western Blot or by ELISA (R&D Systems, Minneapolis, Minn.). Furthermore, activity of the CD8+ supernatants against HIV-1 replication in primary macrophages was distinctly different. The chemokine cocktail at 200 ng/ml failed to inhibit HIV-1 Ba-1 in the majority of primary macrophage cultures, even when the same cocktail inhibited entry of Ba-1 into lymphocytes from the same donor. In the same donor macrophages, unfractionated Caf 10 potently inhibited HIV-1 Ba-1 (as well as a primary NSI isolate) in ten sequential macrophage cultures from separate donors. Whole, as well as fractionated K#1 50K supernatants, as well, inhibited Ba-1 as well with the exception of one donor. The poor inhibitory activity of chemokines against Ba-1 entry into macrophages has been reported in the literature and raises the possibility that another receptor is responsible for entry.

It is clear that the inhibitory function of the supernatants from these HVS-transformed CD8+ cell lines efficiently blocks Ba-1 (and NSI) replication in the majority of donor macrophages, even when CC chemokines do not.

To rule out the possibility that the cell supernatant inhibition was due to direct cell toxicity, both trypan blue exclusion and the MTT assay (Promega, Madison, Wis.) were used to monitor lymphocyte and macrophage cell titers respectively. When up to 50% of the media was replaced with the supernatants, no decrease in CD4+ cell counts were observed relative to control media. At concentrations approaching 100% of the conditioned media there was a modest decrease in cell counts. However, no decrease in cell counts was seen with the subsequent screening of active fraction during the purification. There was no toxicity to primary macrophages relative to media with unfractionated or fractionated K#1 50K and Caf 10 supernatants at any of the concentrations tested. These fractions tested for inhibitory activity at the same time as the toxicity assay retained full inhibitory activity.

These observations in cell culture suggested several characteristics regarding CD8+ inhibitory factors. Factors other than the chemokines RANTES, MIP-1α and MIP-1β appeared to be responsible for the inhibitory activity seen with these cell supernatants. Furthermore, inhibitory activity in each of the characterized cell lines had a unique profile suggesting that there were multiple factors.

Figure 7:
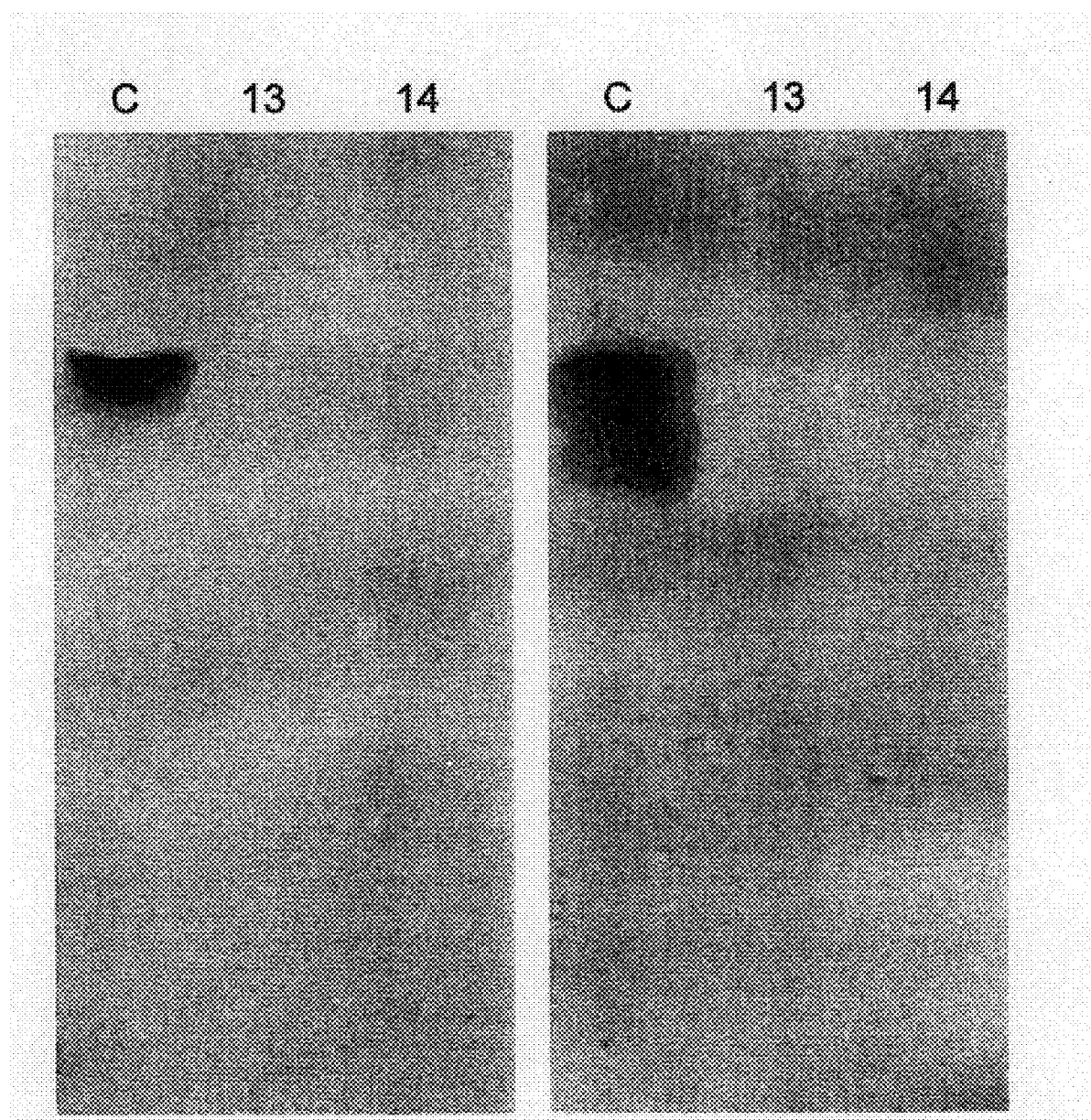
FIG. 7. Analysis of K#1 50K inhibitory fractions for the presence of chemokines.

Further purification of the inhibitory factor(s) has involved the two cell lines, Caf 10, isolated from an HIV-1 infected child with rapid progression and the second line, K#1 50K, isolated from a healthy donor. Each of the cell lines was expanded in tissue culture to 4–5 liters prior to purification of the supernatants. At each step of purification, fractions were tested for inhibitory activity. Each fraction was screened for the ability to inhibit infection of primary macrophages with HIV-1 Ba-1. Ba-1 and primary macrophages were used to screen activity because this activity was consistently the strongest in unfractionated supernatants and differed from the activity of RANTES, MIP-1α and MIP-1β, as described above. Sequential concentration of the CD8+ supernatant and purification by size fractionation, ion-exchange chromatography, followed by reverse-phase chromatography, was performed with both supernatants. Specifically after expanding K#1 50K to 4 liters, the cells were grown for four days to a density of $1 \times 10^6$ cells/ml in serum free RPMI 1640 without phenol red (RPMI-1640, Gibco Scientific, Gaithersburg, Md.) supplemented with I1-2, as well as insulin, transferrin (5 ng/ml) and sodium selenium (Sigma, St. Louis, Mo.). Cells were removed from medium by centrifugation and filtering through 0.22 $\mu$m cellulose acetate filters. The cell conditioned supernatant medium was concentrated by shell freezing 200 ml aliquots in 600 ml Labconco lyophilization flasks and hand swirling them in an acetone/dry ice bath and lyophilizing to dryness overnight. The lyophilate was dissolved in a total of 90 ml of 20 mM Tris, pH 8, and applied to a Centriprep®30 (Amicon) centrifugal concentrator with a 30 kd nominal molecular weight exclusion limit and centrifuged at 2650 rpm (1450 g) in a Sorvall RC5C centrifuge and Sorvall SH3000 rotor according to the manufacturers instructions (max g-force: 1500). The filtrate of the Centriprep30 was applied to a Centriprep®10 concentrator and centrifuged at 3750 rpm (2500 g). The filtrate of the Centriprep®10 which contained all the activity was collected and diluted fourfold and reapplied to new Centriprep®10 filters in order to extract all the active material. This size fractionation step was added to the protocol to remove unwanted high molecular weight proteins. The filtrate, now at a volume of approximately 450 ml was lyophilized to dryness as described above and redissolved in 20 ml of 20 mM Tris, pH 8. The fractionated and concentrated material was applied in 2 ml aliquots to a MonoQ™ HR 5/5 column from Pharmacia Biotech using a 30 min gradient of 0 to 300 mM NaCl in 20 mM Tris, pH 8. The active fractions from the ion exchange runs were pooled, acidified with 0.1% trifluoroacetic acid (TFA) and further fractionated in 2 ml aliquots on a 220×4.6 mm Brownlee™ C2/C18 column from Applied Biosystems on a BioCad Sprint™ from Perceptive Biosystems using a 20 minute gradient of 0 to 70% acetonitrile in 0.1% TFA. Peaks of similar retention volume were pooled and tested for activity. At each step, inhibitory activity was confirmed by monitoring HIV p24 protein levels in virus-infected cells. After ion exchange chromatography, HIV-1 Ba-1 inhibitory fractions (#13 and 14) from K#1 50K were separated on an SDS-polyacrylamide gel and transferred along with recombinant MIP-1 a and RANTES in the left and right control lanes (C) respectively. The blot was stained with antibody to MIP-1α or RANTES (R&D Systems, Minneapolis, Minn.). There was no evidence of either of these chemokines in these fractions (FIG. 7).

Figure 8:
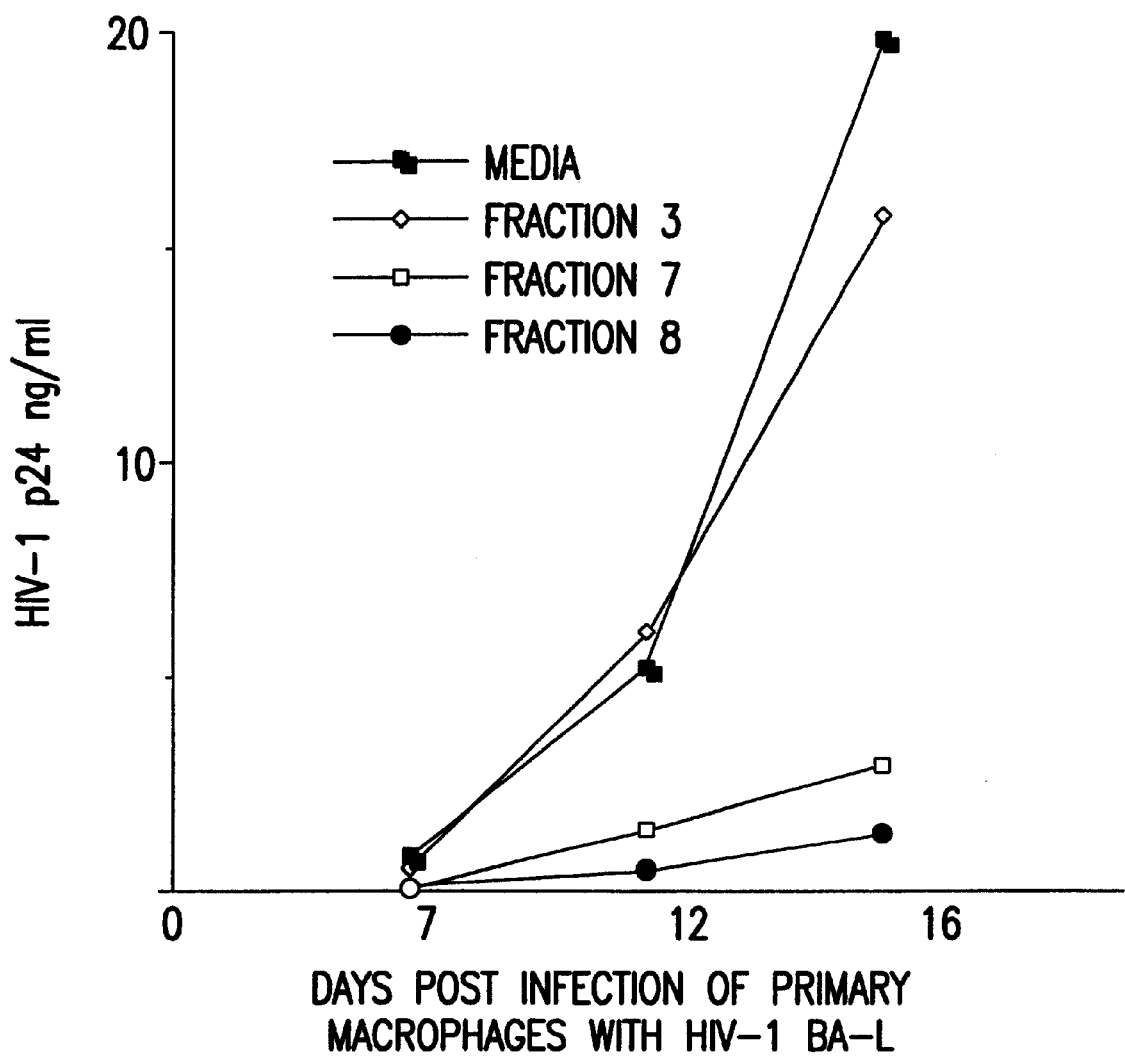
FIG. 8. Inhibition profiles of specific fractions obtained from K#1 50K cells.

In fractions from the final reverse-phase chromatography, activity was retained in several fractions with at least two sequential fractions (fraction 7 and 8) retaining inhibitory activity compared to fraction 3 with no activity (FIG. 8).

Figure 9:
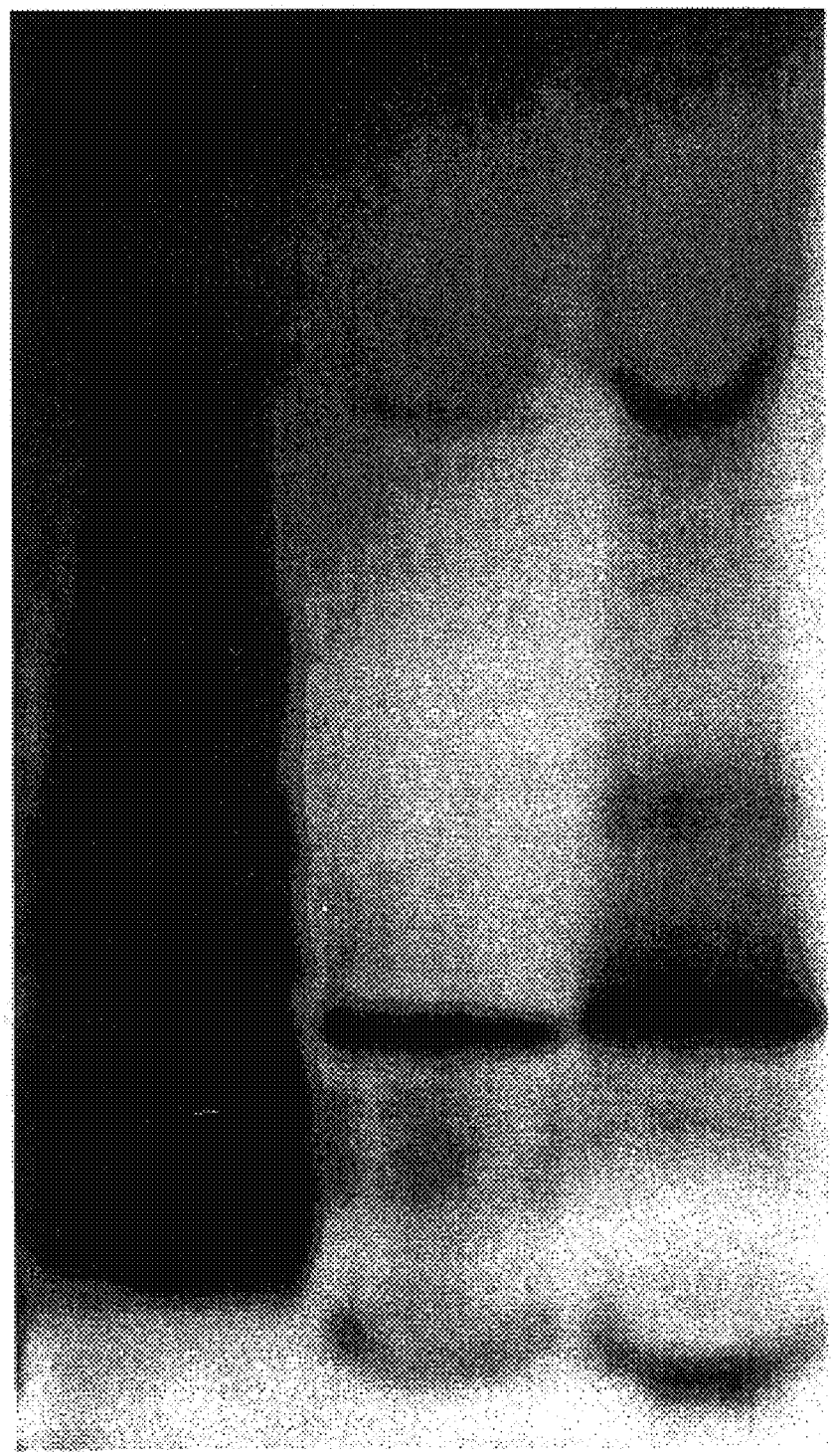
FIG. 9. Protein composition of inhibitory fraction isolated from K#1 50K cells.

Although there was inhibitory activity in other fractions, this active peak contained a single band on an SDS gel. The size of the single band is approximately 8 kd (FIG. 9). Full Ba-1 inhibitory activity was retained in a concentration of approximately 30 pg based on total protein concentration of the active fractions. This level of activity is in contrast to that of RANTES, MIP-1α and MIP-1β as well as to the recently described MDC. The former are active in the ng range in CD4+ cell assays and in the several hundred to 1000 ng range when activity has been seen in macrophages. Native MDC was reported to have inhibitory activity in the 200 ng to 10 μg range (Pal et al., Science 278:695–698, 1997). The activity of the inhibitor is stable at pH 2 and maintains activity after being subjected to freezing and thawing. In collaboration with the core protein laboratory at Rockefeller University, a partial amino acid sequence (19 amino acids) of the purified fraction was obtained. Further sequencing identified the amino acid sequences EQVEASVAS (SEQ. ID NO. 1) and EQVEASVASVRSLY (SEQ. ID NO. 2). The same sequence of the terminal 9 amino acids was obtained on a second sequencing attempt utilizing active material purified under the same conditions containing a single band of the same size as the first by 15% PAGE. The obtained sequence had no significant homology with any known protein sequences. BLAST searches were done of GenBank peptide databank, 3-Dimensional structure Brookhaven Protein Data Bank, Swiss-Prot sequence databank, the PIR databank. In addition the Tentative Human Consensus sequences (THCs) bank was searched in the same manner. THCs have been generated by the Institute for Genomic Research (TIGR) by assembly of Expressed Sequence Tags (ESTs) into virtual transcripts. ESTs are described as partial, single-pass sequences from either end of a cDNA clone and this databank was established to allow rapid identification of expressed genes. Specifically, there was no sequence homology with the recently described HHV-8 chemokine-like protein, vMIP-II, nor with the human chemokine, MDC. As noted below, several lines of evidence are consistent with the HVS-transformed cell derived factor as unique from those previously described.

The small amounts of purified native polypeptide did not allow for extensive biologic testing of the single polypeptide beyond the HIV-I Ba-1 inhibition in macrophages. However, a partially purified fraction, containing additional materials (but no measurable RANTES, MIP-1α and MIP-1β) was evaluated. To allow for complete testing, the total protein concentration in each well was approximately 5–10 pg/ml which is 4–5 fold less than the purified polypeptide used in initial Ba-1 inhibitory studies above. The replication of both Ba-1 as well as an NSI primary isolate were significantly inhibited in primary macrophages (up to 94 and 93% respectively). While HIV-1IIIB replication was inhibited in primary CD4+ cells (up to 78%), Ba-1 was not efficiently inhibited (up to 53%) and the NSI isolate was not inhibited. Although a simple explanation for these findings might be that the concentration of the polypeptide was below the inhibitory threshold for CD4+ cells, it also suggests that target cell-specific characteristics might be playing a role.

Initial experiments to address the mechanism of action of the purified polypeptide were performed. Purified polypeptide was used to treat HIV-1 Ba-1 infected macrophages at 2 hours post-infection. The approximate protein concentration was 50–100 pg/ml. Total macrophage cellular DNA was harvested 2 days post-infection. While DNA amplification by PCR using HIV-specific primers designed to detect circular forms of HIV DNA did not detect any HIV DNA in the treated cells, the untreated cells exhibited clear bands consistent with HIV DNA.. Because the circular forms are seen only upon nuclear import of reverse-transribed HIV DNA, this suggests that the inhibitory polypeptide acts within the period of the viral life cycle from entry of the virus to nuclear import. Further analysis of the extracted DNA showed the presence of reverse-transcribed DNA. It appears that the polypeptide is inhibiting a step in the virus life cycle following reverse transcription but before integration into the cellular genome.

EXAMPLE 5

Generation of Specific Reagants

The partial amino acid sequence of the purified polypeptide described in Example 3 was also used to generate a 10 amino acid synthetic peptide. This has been conjugated to KLH (Pierce) used to immunize rabbits and mice. Immune rabbit and mouse sera specifically recognizes the original peptide sequence in an ELISA assay. The polyclonal antibody partially blocks (50%) the K#1 50K supernatant HIV-1 inhibitory activity. Dot blot hybridization utilizing the immune sera against whole unfractionated supernatants from the cell lines K#1 50K, Caf 10 and K#2sc- and the active fractions of K#1 50K demonstrated hybridization only with K#1 50K unfractionated and active fractions. Although purification of the IgG fraction of the immune sera has resulted in a decrease of background recognition of *E. coli* proteins, background still existed. The immune sera is evaluated for specificity, and, if appropriate, a monoclonal antibody is derived by standard techniques (e.g., Kohler et al., Nature 256:495–497, 1975).

EXAMPLE 6

Identification and Closing of the Active Polypeptide

A cDNA library has been generated utilizing polyA-selected RNA extracted from the original HVS-transformed cell line, K#1 50K. This was cloned into the vector Lambda TriplEX (Clontech, Palo Alto, Calif.) which allows screening with the DNA probe as well as expression cloning with the antibody. The library has >$10^9$ plaque forming units/ml.

A mix of degenerate nucleotide primers encoding the original amino acid sequence have been used to amplify DNA sequences by PCR. Candidate cDNA clones are used to screen for HIV-1 inhibitory activity utilizing a transient transfection strategy. The cDNAs are cloned into the mammalian expression vector pSecTag Xpress (Invitrogen) under the control of the CMV promoter. This vector allows purification directly from the cell supernatant utilizing the C-terminal fusion with an anti-myc or anti-His antibody. The vector also contains the Zeocin resistance gene to allow for rapid selection of mammalian (as well as bacterial) cells. Cell lines with little baseline activity (such as the human embryonic kidney 293 cells) are transfected with the cDNA (with selection to enhance the number of expressing cells). Cell supernatant is tested utilizing the same functional assays as used for the original screening of the CD8+ supernatants. This includes testing for activity against HIV-1 Ba-1 and IIIB in primary macrophages and CD4+ cells, respectively, as well as against a panel of SI and NSI isolates in the laboratory. This is done with and without preabsorption of the supernatants with the polyclonal rabbit antisera.

The supernatants are screened for the presence of the protein by immunoblotting using the rabbit polyclonal antibody as well. If significant activity is obtained, this cDNA is cloned into a bacterial expression vector for expression and purification of the inhibitory polypeptide.

Parallel to the cloning process, large scale isolation and purification of K#1 50K native polypeptide is undertaken with modifications of both the cell culture conditions as well as the protein purification to increase the yield. The process can be scaled up to 10–15 liters using suspension 3 liter culture flasks with stir bars. To fractionate approximately 4 times the volume of material requires modifications to the previously described purification scheme. Initial fractionation is done using a Mintan™ high resolution tangential flow system with a 10 kd nominal molecular weight cut off low protein binding regenerated cellulose filter sheet. This system from Millipore has two high capacity peristaltic pumps and allows the throughput of large volumes of material in a short period of time. Once again, this step is required to remove most of the unwanted high molecular weight proteins prior to the chromatography steps and limits their involvement in formation of precipitation complexes that cannot be redissolved after lyophilization. Primary concentration is again done by freeze drying and redissolving in about 400 ml of 20 mM Tris, pH 8, buffer. To prepare the fractionated and concentrated material for chromatography it is dialysed through 3.5 kd molecular weight cutoff membrane against 100 fold excess of chromatography buffer over a period of 16 hours at 4° C. This step places the material in the optimal ionic and pH condition for chromatography and rapidly removes most of the contaminating amino acids present in the cell growth medium. Total proteins from the prepared material are captured in a single loading on a Pharmacia HiLoad™ Q 16/10 Fast Flow column. The resin of this column is of average diameter (90 $\mu$m) and allows high flowrate throughput of material and has the same ligand chemistry, and hence binding capacity, as the smaller MonoQ column previously used as first capture column. However, the HiLoad™ column has poorer resolution than the MonoQ, but is very useful as first step capture column and gives a defined well separated peak that contains all the biologic activity. From pilot studies, the active peak is predicted to be about 10 ml in volume. To resolve the individual proteins into separate peaks, the HiLoad™ capture peak is applied to a 6 ml MonoQ column in a single superloop loading and eluted with a shallow gradient 0–300 mM NaCl over 40 minutes. The active peak from the high resolution Q column is acidified as before with 0.1% trifluoroacetic acid (TFA) and applied to a 4.6/250 mm Sephasil C18 column from Pharmacia and developed with a 30 minute 0–70% acetonitrile gradient in the presence of 0.1% TFA. This modified purification protocol reduces the number of lyophilization and dialysis steps and reduces the losses incurred during these steps. Further losses have been shown to be avoided by size fractionation prior to lyophylization and by large scale capture in single load rather than separate small aliquots. This allows for purification of ng quantities of the polypeptide. Larger quantities of the native purified polypeptide allows complete biologic characterization that was not possible in light of the small quantities obtained from the first purifications (pgs) and the initial priority to obtain amino acid sequence. The native polypeptide is gel purified, eluted and tested against IIIB, Ba-1 and a panel of primary isolates in primary CD4+ cells and macrophages and is screened in the U1 assay.

EXAMPLE 7

Production and Purification of the Inhibitory Protein in a Bacterial Expression System For large scale purification of the polypeptide, a cDNA encoding the polypeptide is cloned into the bacterial expression vector pTrcHis A,B,C (Invitrogen, San Diego, Calif.). This vector allows high level expression in *E. coli* with fusion of the polypeptide product to both histidine residues for purification, as well as a myc epitope for detection. Purification uses the nickel-chelating resin, ProBond (Invitrogen) with subsequent elution and removal of the histidine fusion peptide with enterokinase cleavage. Activity of the bacterial-purified polypeptide is compared to the small preparation from mammalian cell purification to determine if full activity is retained in the recombinant bacterial polypeptide. Inhibition of laboratory and primary viral isolates is compared in primary CD4+ cells and macrophages with dose response curves ranging from pg to $\mu$g concentrations. If the recombinant polypeptide has the same inhibitory profile as the native polypeptide, this preparation is used for subsequent studies defining the level of inhibition.

What is claimed is:

1. An inhibitor of HIV replication, comprising a peptide or polypeptide having the amino acid sequence of SEQ. ID NO. 1.

2. An inhibitor of HIV replication, comprising a peptide or polypeptide having the amino acid sequence of SEQ. ID NO. 2.

* * * * *

UNITED STATES PATENT AND TRADEMARK OFFICE
CERTIFICATE OF CORRECTION

PATENT NO. : 6,358,511 B1
DATED : March 19, 2002
INVENTOR(S) : Klotman et al.

It is certified that error appears in the above-identified patent and that said Letters Patent is hereby corrected as shown below:

Title page, Item [54] and Column 1, line 1,
Title, "INHIBITORS OF HIV INFECTION" should read -- PEPTIDE OR POLYPEPTIDE INHIBITORS OF HIV-1 INFECTION --

Title page,
Item [75], Inventor(s), "Mosoian Arevik" should read -- Arevik Mosoian --; and "Teixeira Avelino" should read -- Avelino Teixeira --
Insert: -- [63] Related U.S. Application Data, 60/084076 May 4, 1998 --

Column 4,
Line 45, "IIe" should read -- Ile --
Line 59, "subtantially" should read -- substantially --

Column 5,
Line 31, "chomatography" should read -- chromatography --
Line 42, "ficoll-hapague" should read -- Ficoll-Hapague --
Line 56, "inihibiting" should read -- inhibiting --
Line 67, "reagants" should read -- reagents --

Column 6,
Line 5, "reagants" should read -- reagents --
Line 11, "screenning" should read -- screening --
Line 13, "inibitory" should read -- inhibitory --

Column 8,
Line 40, "asym-" should read -- asymp- --

Column 10,
Line 3, "transcriptatse" should read -- transcriptase --
Line 56, "e.g," should read -- e.g., --

Column 11,
Line 6, ">500/mm3." should read -- >500/mm$^3$. --
Line 39, "ficoll-hapague" should read -- Ficoll-Hapague --
Line 58, "macrophage" should read -- macrophage -- -

UNITED STATES PATENT AND TRADEMARK OFFICE
CERTIFICATE OF CORRECTION

PATENT NO. : 6,358,511 B1
DATED : March 19, 2002
INVENTOR(S) : Klotman et al.

It is certified that error appears in the above-identified patent and that said Letters Patent is hereby corrected as shown below:

Column 12,
Line 4, "Dupont" should read -- DuPont --
Line 62, "Know" should read -- Known --

Column 13,
Table 1, "Rantes" should read -- RANTES --

Column 14,
Line 25, "I1-2" (I one-two) should read -- Il-2 -- (I lowercase "L"-two)
Line 63, "MIP-1 a" should read -- MIP-1α --

Column 16,
Line 5, "DNA.." should read -- DNA. --
Line 6, "reverse-transribed" should read -- reverse-transcribed --
Line 16, "Reagants" should read -- Reagents --

Signed and Sealed this

Fifth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO.         : 6,358,511 B1
APPLICATION NO. : 09/305781
DATED              : March 19, 2002
INVENTOR(S)        : Mary E. Klotman, Mosoian Arevik and Teixeira Avelino It is certified that error appears in the above-identified patent and that said Letters Patent is hereby corrected as shown below:

IN THE SPECIFICATION:
Please insert, before Col. 1, line 3 ("INTRODUCTION"), the following paragraph:

-- This invention was made with government support under NIH grant number AI-43698 awarded by the National Institutes of Health. The United States Government has certain rights in the invention. --

Signed and Sealed this

Twenty-second Day of September, 2009

David J. Kappos
*Director of the United States Patent and Trademark Office*